Figure 1:
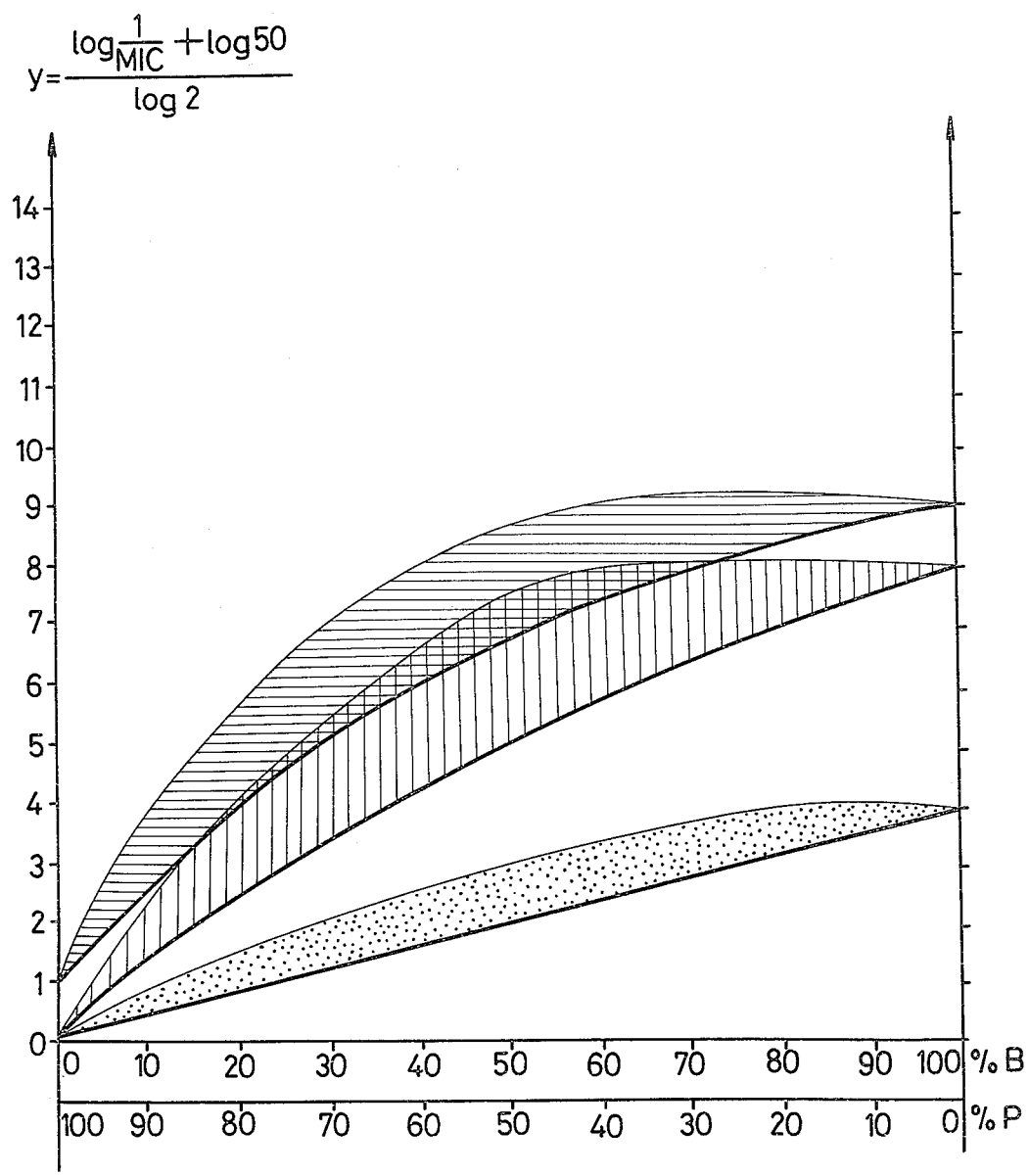

United States Patent [19]

Pfliegel et al.

[11] 4,305,953

[45] Dec. 15, 1981

[54] SYNERGISTIC FUNGICIDAL COMPOSITIONS

[75] Inventors: Tódor Pfliegel; Erzsebet Radvanyi née Hegedus; Gizella Hamar nee Nemes, all of Budapest; András Frankó; Lajos Ferenczy, both of Szeged, all of Hungary

[73] Assignee: Chinoin Gyógyszer és Végyeszeti Termékek Gyára RT, Budapest, Hungary

[21] Appl. No.: 143,611

[22] Filed: Apr. 25, 1980

[30] Foreign Application Priority Data

Apr. 27, 1979 [HU] Hungary .............................. CI 1929

[51] Int. Cl.³ .................... A01W 43/56; A01W 43/50; A61K 31/415
[52] U.S. Cl. .............................. 424/273 B; 424/273 R
[58] Field of Search ....................... 424/273 R, 273 B

[56] References Cited

PUBLICATIONS

The Merck Index, 9th Ed., 1976, Merck & Co., Inc., Rahway, N. J. p. 135.
Chemical Abstracts 86:1093v (1977).

*Primary Examiner*—Jerome D. Goldberg
*Attorney, Agent, or Firm*—Karl F. Ross

[57] ABSTRACT

The invention relates to new synergistic fungicidal compositions comprising a mixture of (a) methyl 2-benzimidazolecarbamate or a precursor thereof, such as methyl 1-(butylcarbamoyl)-2-benzimidazolecarbamate and 1,2-bis(3-methoxy-carbonyl-2-thioureido)benzene and (b) 1H-α-butyl-α-phenylimidazol-1-yl-propanenitrile.

4 Claims, 4 Drawing Figures

▭ Botrytis cinerea
▥ Epidermophyton flocosum
▨ Fusarium moniliforme

The antagonistic response of a combination of carbendazime and promidion

- Ascochyta pisi
- Cercospora beticola
- Stemphylium radicinum

The synergistic effect of a combination of benomyl and fenapronil (phitopathogenic fungi)

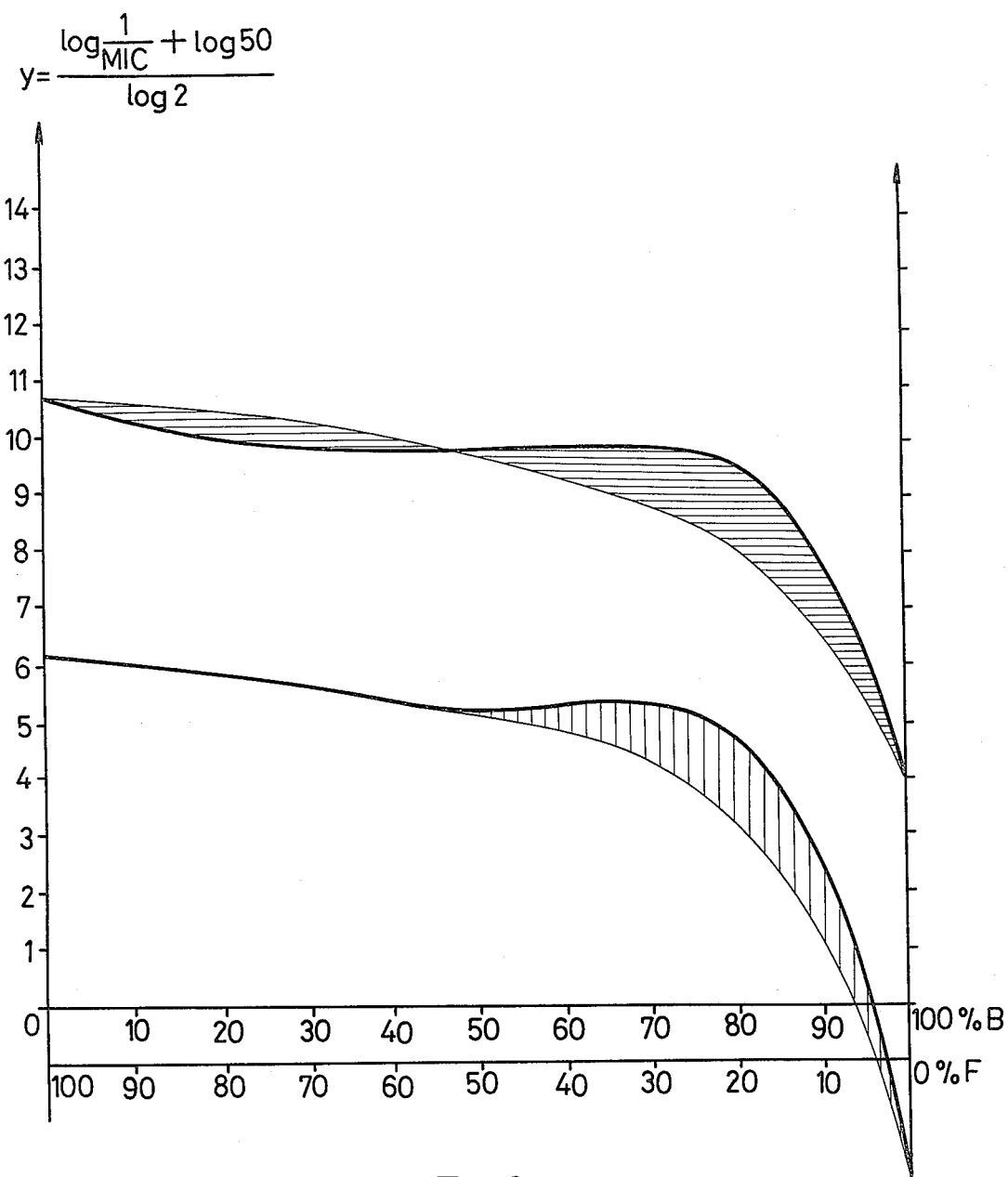
Fig. 3
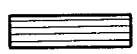 Trichophyton rubrum
 Candida utilis
Synergistic effect of a combination of benomyl and fenapronil (human and animal pathogenic fungi)

A ──o──o──
B ─ ─ ─ ─ ─ ─
C ──×──×──
D ──·──·──·── various benomyl-resistant Botrytis cinerea strain

Combination of benomyl and fenapronil against for benomyl resistant Botrytis cinerea strain

SYNERGISTIC FUNGICIDAL COMPOSITIONS

The invention relates to new synergistic fungicidal compositions. More particularly, the invention concerns synergistic fungicidal compositions comprising a mixture of (a) methyl 2-benzimidazolecarbamate or a precursor thereof and (b) 1H-α-butyl-α-phenylimidazol-1-yl-propanenitrile.

The systemic fungicides generally attack fungi in a single center of activity. Therefore, within a relatively short time after the introduction of a new systemic fungicide, fungi become tolerant or even resistant, which is a constantly recurring problem in agriculture.

The activities of more different compositions containing a combination of two systemic fungicides in various mutual proportions were tested against various fungi. Evaluation was carried out on the basis of minimum concentration causing total inhibition (MIC) expressed in μg/ml. The theoretical value of MIC was calculated on the basis of the following equation:

$$\frac{m_A}{MIC_A} + \frac{M_B}{MIC_B} = \frac{1}{MIC_{(m_A+m_B)}}$$

wherein $m_A$: weight fraction of component "A"
$m_B$: weight fraction of component "B"
$m_A + m_B = 1$
$MIC_A$: minimum inhibition concentration of component "A"
$MIC_B$: minimum inhibition concentration of component "B"

The calculated $MIC_{(m_A+m_B)}$ value was then compared with the found $MIC_{(m_A+m_B)}$ value and the extent of interaction was calculated on the basis of the ratio $MIC_{calculated}/MIC_{found}$. The interaction was called antagonistic, if this ratio was less than 1; additive, if the ratio was about 1; and synergistic, if the ratio was greater than 1. In some cases the results were also graphically represented, where the $$y = \frac{\log \frac{1}{MIC} + \log 50}{\log 2}$$

values were plotted agains the mutual proportions of the fungicidal components.

At first an anti-mycosis agent, carbendazime (methyl 2-benzimidazolecarbamate) and precursors thereof e.g. benomyl [methyl 1-(butylcarbamoyl)-2-benzimidazolecarbamate] and thiophanate-methyl [1,2-bis(3-methoxycarbonyl-2-thioureido)benzene] [Clemons, G. P., Sisler, H. D. (1971) Pesticide Biochem. Physiol. 1, 32] were combined with two systemic fungicides, namely promidion [3-(3,5-dichlorophenyl)-2,4-dioxo-1-(N-isopropyl)-imidazolinecarboxamide] [May and Baker, U.S. Pat. No. 3,755,350] and vinclosolin [3-(3,5-dichlorophenyl)-5-methyl-5-vinyl-1,3-oxazolidine-2,4-dione] [BASF, U.S. Pat. No. 3,966,750], which supposedly have different modes of action. Though all details of the modes of action are not known yet, it has been proved that both systemic fungicides induce an accumulation of fatty acids and triglycerides in fungi which are sensitive to them [Fritz, R., Leroux, P., Gredt, M. (1977) Phytopathol. Z. 90 (2) 152].

A strong antagonistic effect was observed in both cases (see Examples 1 and 2 and FIG. 1).

We have thereafter turned to the fungicides, inhibiting lipid and sterol synthesis (which have just the opposite activity than the fungicides tested hereinbefore), e.g. triadimefon [1-(4-chlorophenoxy)-3,3-dimethyl-1-(1H)-(1,2,4-triazol-1-yl)buthan-2-one] [Bayer, U.S. Pat. No. 3,912,752; Kaspers H. et al (1975) 8th Int. Plnt. Prot. Congr. (Moscow), Part II, p. 388] and Phenapropyl [Rohm and Haas, DOS No. 2,430,039; Martin, R. A., Edgington, L. V. (1978) 4th IUPAC Congr. Pesticide Chem. (Zürich) Abstr. IV-7].

Triadimefon is very potent but has a comparatively narrow scope of activity; thus first is effective against obligate parasites such as real powdery mildew, blight, rust etc. but is entirely ineffective against the fungi tested in vitro in the present application. Its mixtures with carbendazime and precursors thereof showed an essentially additive effect (see Example 3). Results obtained against powdery mildew in vivo are presented in Example 5.

Figure 2:
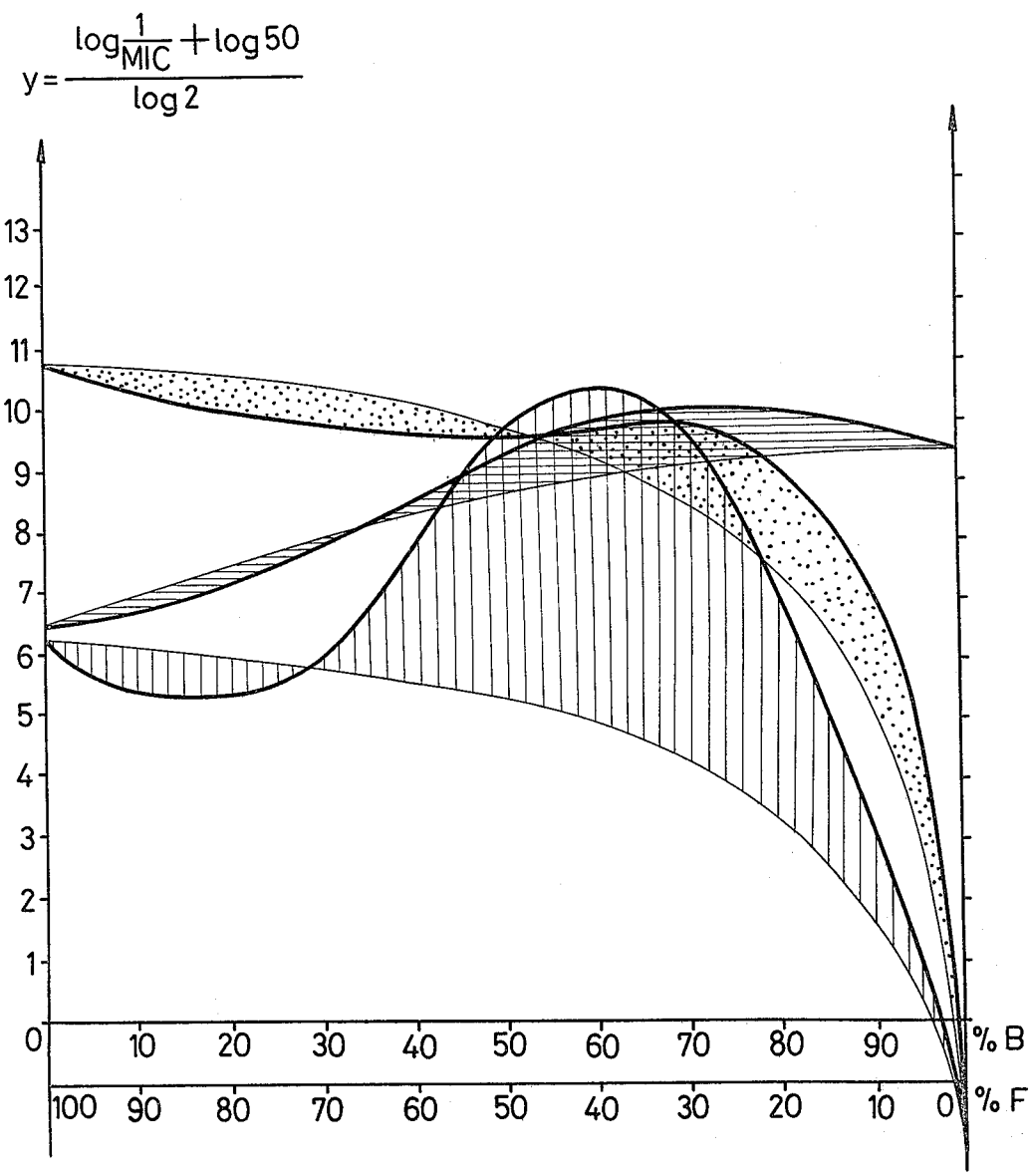

It has surprisingly been found that fenapronil which is extremely potent alone and has a wide field of activity, in vitro shows a strong synergistic activity in combination with carbendazime and the precursors therefor (see Example 4 and FIGS. 2 and 3). The results of tests carried out in vivo on powdery mildew are outlined in Example 6.

Figure 4:
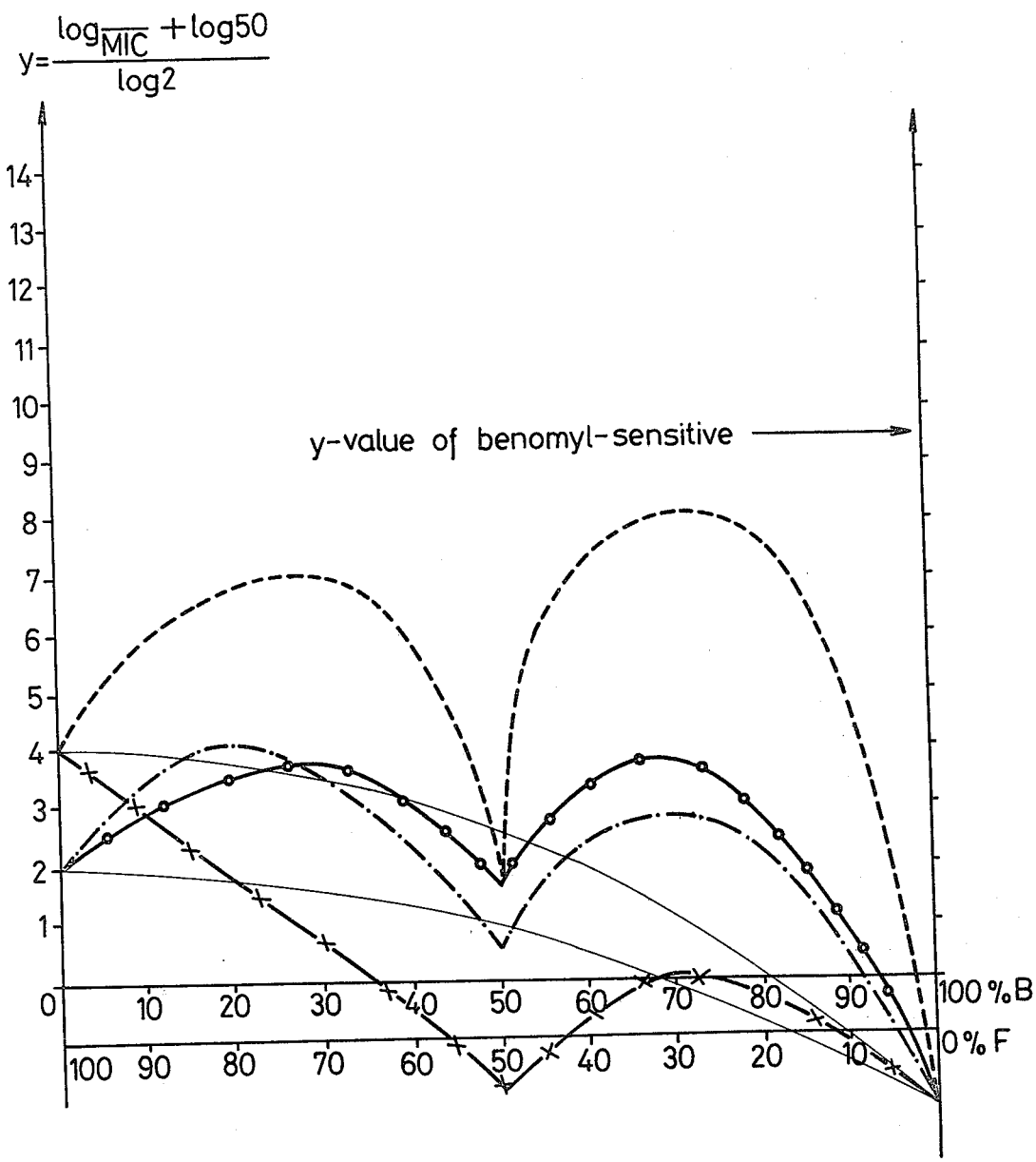

It has further been found that the synergistic activity is unexpectedly maintained also when a strain of the fungus examined has become resistant against carbendazime or a precursor thereof (see FIG. 4).

This unexpected synergism has a great practical importance since, in addition to the widening of the scope of activity, and to the prolongation of the development of resistance, or even the total elimination thereof, the effective doses are lower than the doses required separately.

Since a synergistic activity was observed on plant, human and animal pathogenic fungi, the synergistic active ingredient combination can be transformed into plant protecting and pharmaceutical compositions as well.

The invention relates to synergistic fungicidal compositions comprising a mixture of (a) methyl 2-benzimidazolecarbamate or a precursor thereof, and (b) 1H-α-butyl-α-phenylimidazol-1-yl-propanenitrile, optionally in admixture with conventional, inert, compatible carriers, surface active agents and optionally further conventional additives.

Preferred precursors for methyl 2-benzimidazolecarbamate are methyl 1-(butylcarbamoyl)-2-benzimidazolecarbamate and 1,2-bis(3-methoxycarbonyl-2-thioureido)-benzene.

For plant protecting use the preferred formulations are emulsifiable concentrates, wettable powders suitable for spraying or seed dressing, liquid pastes etc.

Pharmaceutical compositions can be formulated as ointments, oily solutions, suspensions, powders etc.

The mutual proportions of the two active ingredients in the compositions according to the invention are between 1:9 and 9:1, preferably 1:1 and 9:1 (weight).

The total concentration of the active ingredients is from 0.5 to 90% by weight, preferably 0.5 to 50% by weight.

The following Examples provide further illustration demonstrating the synergistic fungicidal activity of the present compositions.

EXAMPLE 1

This example demonstrates the antagonistic character of a mixture of carbendazime and promidion against various fungi. Carbendazime was used as a chemical substance, and promidion as a formulation Rovral 50 WP in a concentration of 200 μg./ml. calculated for active ingredient. The combination of carbendazime and the formulation containing promidion were dissolved in dimethyl sulfoxide and the solution was added into a yeast extract agar having a pH of 7.2. The maximum concentration of dimethyl sulfoxide was 1%. From the concentrate obtained a series of various dilutions was prepared. The culture medium was sterilized, filled into Petri-dishes, solidified and injected with spore suspensions of the test fungi. The dishes were incubated at 22° to 25° C. for 4 to 5 days and the minimum inhibition concentration (MIC) was determined (μg./ml.).

The results of these tests are listed in Table I.

TABLE I

| | MIC (ug./ml.) | | $MIC_{calc.}/$ |
|---|---|---|---|
| | calculated | found | $MIC_{found}$ |
| *Botrytis cinerea* | | | |
| carbendazime | — | 0.07 | — |
| promidion | — | 25 | — |
| carbendazime + promidion 1:1 | 0.14 | 0.7 | 0.20 |
| *Fusarium moniliforma* | | | |
| carbendazime | — | 3 | — |
| promidion | — | 50 | — |
| carbendazime + promidion 1:1 | 5.66 | 12 | 0.47 |
| *Epidermophyton floccosum* | | | |
| carbendazime | — | 0.15 | — |
| promidion | — | 50 | — |
| carbendazime + promidion 1:1 | 0.30 | 1.5 | 0.20 |

EXAMPLE 2

This example demonstrates the antagonistic effect of a mixture of benomyl and vinclosolin. Benomyl was introduced into the culture medium in the form of Fundazol 50 WP and vinclosolin as a formulation Ronilan 50 WP. As a diluent water was used. Further on following the procedure of Example 1 the following results were obtained.

TABLE II

| | MIC (μg./ml.) | | $MIC_{calc.}/$ |
|---|---|---|---|
| | calculated | found | $MIC_{found}$ |
| *Botrytis cinerea* | | | |
| benomyl | — | 0.07 | — |
| vinclosolin | — | 50 | — |
| benomyl + vinclosolin 1:1 | 0.14 | 0.7 | 0.20 |
| *Scelerotinia sclerotiorum* | | | |
| benomyl | — | 0.03 | — |
| vinclosolin | — | 0.3 | — |
| benomyl + vinclosolin 1:1 | 0.05 | 0.07 | 0.78 |
| *Trichophyton mentagrophytos* | | | |
| benomyl | — | 0.7 | — |
| vinclosolin | — | 50 | — |
| benomyl + vinclosolin 1:1 | 1.38 | 3 | 0.46 |
| *Aspergillus niger* | | | |
| benomyl | — | 0.7 | — |
| vinclosolin | — | 25 | — |
| benomyl + vinclosolin 1:1 | 1.36 | 1.5 | 0.91 |

EXAMPLE 3

This example demonstrates the essentially additive response of a mixture of carbendazime and triadimefon. Both active ingredients were used per se, i.e. as active substances, otherwise the procedure described in Example 1 was followed. The results are set forth in the following table.

TABLE III

| | MIC (μg./ml.) | | $MIC_{calc.}/$ |
|---|---|---|---|
| | calculated | found | $MIC_{found}$ |
| *Botrytis cinerea* | | | |
| carbendazime | — | 0.07 | — |
| triadimefon | — | >300 | — |
| carbendazime + triadimefon 1:1 | 0.14 | 0.3 | 0.47 |
| *Sclerotinia sclerotiorum* | | | |
| carbendazime | — | <0.03 | — |
| triadimefon | — | >300 | — |
| carbendazime + triadimefon 1:1 | 0.06 | 0.07 | 0.85 |
| *Aspergillus niger* | | | |
| carbendazime | — | 0.7 | — |
| triadimefon | — | >300 | — |
| carbendazime + triadimefon 1:1 | 1.40 | 1.5 | 0.93 |
| *Trichophyton mentagrophytes* | | | |
| carbendazime | — | 0.7 | — |
| triadimefon | — | >300 | — |
| carbendazime + triadimefon 1:1 | 1.40 | 1.5 | 0.93 |
| *Epidermophyton floccosum* | | | |
| carbendazime | — | 0.15 | — |
| triadimefon | — | >300 | — |
| carbendazime + triadimefon 1:1 | 0.30 | 0.3 | 1 |

EXAMPLE 4

This example demonstrates the synergistic activity of various mixtures of benomyl (in the form of Fundazol 50 WP) and fenapronil (Systane 25 EC). Using aqueous dispersions of the active substance and following the procedure described in Example 1 the results set forth in Table IV have been obtained. The results are graphically illustrated on FIGS. 2 and 3.

The extent of synergism generally is about 2 but a synergism of about 40 was observed in the case of *Stemphylium radicinum*, while against *Aspergillus niger* the effect was essentially additive.

TABLE IV

| | MIC (μg./ml.) | | $MIC_{calc.}/$ |
|---|---|---|---|
| | calculated | found | $MIC_{found}$ |
| *Alternarin tenuis* | | | |
| benomyl | — | >300 | — |
| fenapronil | — | 0.07 | — |
| benomyl + fenapronil 2:1 | 0.21 | 0.11 | 1.93 |
| benomyl + fenapronil 1:1 | 0.14 | <0.06 | 2.33 |
| benomyl + fenapronil 1:2 | 0.10 | 0.05 | 2.00 |

TABLE IV-continued

| | MIC (μg./ml.) | | MIC$_{calc.}$/ |
|---|---|---|---|
| | calculated | found | MIC$_{found}$ |
| *Stemphylium radicinum* | | | |
| benomyl | — | >300 | — |
| fenapronil | — | 0.7 | — |
| benomyl + fenapronil 2:1 | 2.12 | 0.05 | 42.40 |
| benomyl + fenapronil 1:1 | 1.40 | 0.06 | 29.27 |
| benomyl + fenapronil 1:2 | 1.04 | 1 | 1.04 |
| *Cercospora beticola* | | | |
| benomyl | —0.07 | — | |
| fenapronil | — | 0.6 | — |
| benomyl + fenapronil 2:1 | 0.10 | <0.05 | 2.0 |
| benomyl + fenapronil 1:1 | 0.13 | <0.06 | 2.09 |
| benomyl + fenapronil 1:2 | 0.17 | 0.22 | 0.78 |
| *Ascochyta pisi* | | | |
| benomyl | — | 6 | — |
| fenapronil | — | <0.03 | — |
| benomyl + fenapronil 2:1 | 0.09 | <0.05 | 1.80 |
| benomyl + fenapronil 1:1 | 0.06 | <0.06 | 1.0 |
| benomyl + fenapronil 1:2 | 0.04 | <0.05 | 0.80 |
| *Phytophthora infestans* | | | |
| benomyl | — | >300 | — |
| fenapronil | — | 12 | — |
| benomyl + fenapronil 2:1 | 33.63 | 24 | 1.40 |
| benomyl + fenapronil 1:1 | 23.07 | 12 | 1.92 |
| benomyl + fenapronil 1:2 | 17.56 | 9 | 1.95 |
| *Aspergillus niger* | | | |
| benomyl | — | 6 | — |
| fenapronil | — | 0.3 | — |
| benomyl + fenapronil 2:1 | 0.82 | 1 | 0.82 |
| benomyl + fenapronil 1:1 | 0.57 | 0.6 | 0.95 |
| benomyl + fenapronil 1:2 | 0.44 | 1 | 0.44 |
| *Trichophyton rubrum* | | | |
| benomyl | — | 3 | — |
| fenapronil | — | <0.03 | — |
| benomyl + fenapronil 2:1 | 0.09 | <0.05 | 1.78 |
| benomyl + fenapronil 1:1 | 0.06 | <0.06 | 1.00 |
| benomyl + fenapronil 1:2 | 0.04 | <0.05 | 0.89 |
| *Candida utilis* | | | |
| benomyl | — | >300 | — |
| fenapronil | — | 0.7 | — |
| benomyl + fenapronil 2:1 | 1.11 | 1 | 2.11 |
| benomyl + fenapronil 1:1 | 1.40 | 1.5 | 0.93 |
| benomyl + fenapronil 1:2 | 1.04 | 1 | 1.04 |

EXAMPLE 5

The in vivo effect of various mixtures of triadimefon 50 WP and benomyl 50 WP was observed against powders mildew (*Erysiphe graminis*). The plants were grown in plots at 20° C., under a relative humidity of 98% for 7 days. The one-week old plant were then sprayed with the test composition and after drying were injected with *Erysiphe graminis*. After incubation for 6 days the results were evaluated.

TABLE V

| Erysiphe graminis concentra- | Extent of infection | | |
|---|---|---|---|
| tion | 3% | 6% | 12% |
| benomyl | 32.2% | 23.3% | 16.3% |
| triadimefon | 73.5% | 66.0% | 40.6% |
| benomyl + triadimefon 1:1 | 51.2% | 29.3% | 16% |

EXAMPLE 6

The procedure described in Example 5 was used but fenapronil 25 EC and benomyl 50 WP were tested. The following results have been obtained.

TABLE VI

| Erysiphe graminis concentra- | Extent of infection | | |
|---|---|---|---|
| tion | 12 ppm | 25 ppm | 50 ppm |
| benomyl | 78% | 64% | 56% |
| fenapronil | 43% | 23% | 14% |
| benomyl + fenapronil 1:1 | 46% | 27% | 16% |

EXAMPLE 7

The effect of various mixtures of benomyl (Fundazol 50 WP) and fenapronil (Systane 25 EC) was observed on *Botrytic cinerea* isolated from four different cultivated plants, which were resistant to benomyl used in a concentration of 200 μg./ml. Though the sensitivity of the different strains was different, it could unambiguously be observed that the 2:1 and 1:2 mixtures showed a very good synergism, while in the case of the 1:1 mixtures the synergism was essentially weaker, moreover, in some instances antagonism was observed. The results are illustrated in the following Table VII.

TABLE VII

| | MIC (μg./ml.) | | MIC$_{calc.}$ |
|---|---|---|---|
| | calculated | found | MIC$_{found}$ |
| *Botrytis cinerea*, strain A | | | |
| benomyl | — | >200 | — |
| fenapronil | — | 15 | — |
| benomyl + fenapronil 2:1 | 39.45 | 3.7 | 10.66 |
| benomyl + fenapronil 1:1 | 27.90 | 15 | 1.86 |
| benomyl + fenapronil 1:2 | 21.59 | 3.7 | 5.84 |
| *Botrytis cinerea*, strain B | | | |
| benomyl | — | >200 | — |
| fenapronil | — | 3.7 | — |
| benomyl + fenapronil 2:1 | 10.80 | 0.2 | 54.03 |
| benomyl + fenapronil 1:1 | 7.27 | 15 | 0.48 |
| benomyl + fenapronil 1:2 | 5.47 | 0.4 | 13.68 |
| *Botrytis cinerea*, strain C | | | |
| benomyl | — | >200 | — |
| fenapronil | — | 3.7 | — |
| benomyl + fenapronil 2:1 | 10.80 | 60 | 0.18 |
| benomyl + fenapronil 1:1 | 7.27 | >200 | 0.04 |
| benomyl + fenapronil 1:2 | 5.47 | 30 | 0.18 |
| *Botrytis cinerea*, strain D | | | |
| benomyl | — | >200 | — |
| fenapronil | — | 15 | — |
| benomyl + fenapronil 2:1 | 39.45 | 7.5 | 5.26 |
| benomyl + fenapronil 1:1 | 27.90 | 30 | 0.93 |
| benomyl + | | | |

TABLE VII-continued

| | MIC (µg./ml.) | | $\text{MIC}_{calc.}$ |
| --- | --- | --- | --- |
| | calculated | found | $\text{MIC}_{found}$ |
| fenapronil 1:2 | 21.59 | 3.7 | 5.84 |

EXAMPLE 8

Wettable powder

A wettable powder containing the following ingredients was prepared by conventional techniques.

| | |
| --- | --- |
| carbendazime | 50 g. (1 to 8 µ) |
| triadimefon | 20 g. (1 to 8 µ) |
| aerosil 300 | 10.5 g. |
| $CaCO_3$ | 9.5 g. |
| Na-alkylpolyglycolether sulfonate | 5 g. |
| Na-lignine sulfonate | 5 g. |

EXAMPLE 9

Paste

A paste containing the following ingredients was prepared by conventional techniques. Benomyl and fenapronil were used in a micronized form.

| | |
| --- | --- |
| benomyl | 20 g. |
| fenapronil | 20 g. |
| 1:1 mixture of sorbitane fatty acid ester and polyoxyethylene-sorbinate fatty acid ester | 8 g. |
| polyvinylpyrrolidone | 2 g. |
| anhydrous glycerine | 50 g. |

EXAMPLE 10

Painting composition

A painting composition containing the following ingredients was prepared by conventional techniques.

| | |
| --- | --- |
| carbendazime | 0.6% |
| fenapronil | 0.4% |
| 96% ethanol | 98% |
| dimethyl sulfoxide | 1% |

EXAMPLE 11

Dusting powder

Benomyl and fenapronil were ground under a grain size of 10µ and a dusting powder was prepared using the following ingredients:

| | |
| --- | --- |
| benomyl | 0.7% |
| fenapronil | 0.3% |
| zinc oxide | 10% |
| magnesium oxide | 89% |

We claim:

1. A synergistic fungicidal composition which comprises as an active ingredient a fungicidally effective amount of a mixture of
   (a) methyl 1-(butylcarbamoyl)-2-benzimidazole-carbamate and
   (b) 1H-α-butyl-α-phenylimidazol-1-yl-propanenitrile, in a respective mutual weight proportion of 1:2 to 2:1 and in admixture with an inert fungicidally compatible carrier.

2. The composition defined in claim 1 in which the total active ingredient concentration is 0.5 to 90% by weight.

3. The composition defined in claim 1 in which the total active ingredient concentration is 0.5 to 50% by weight.

4. A method of controlling fungus diseases of plants, which comprises applying to the plants a fungicidally effective amount of the composition defined in claim 1.

* * * * *